(12) United States Patent
Petersen et al.

(10) Patent No.: US 7,541,024 B2
(45) Date of Patent: Jun. 2, 2009

(54) LOW SALT FORMS OF POLYALLYLAMINE

(75) Inventors: John S. Petersen, Acton, MA (US); Steven K. Burke, Sudbury, MA (US); Stephen Randall Holmes-Farley, Arlington, MA (US)

(73) Assignee: Genzyme Corporation, Cambridge, MA (US)

( * ) Notice: Subject to any disclaimer, the term of this patent is extended or adjusted under 35 U.S.C. 154(b) by 738 days.

(21) Appl. No.: 10/125,684

(22) Filed: Apr. 17, 2002

(65) Prior Publication Data

US 2002/0159968 A1   Oct. 31, 2002

Related U.S. Application Data

(60) Provisional application No. 60/284,445, filed on Apr. 18, 2001.

(51) Int. Cl.
A61K 31/74   (2006.01)
(52) U.S. Cl. .................................................. 424/78.1
(58) Field of Classification Search .................. 424/78.1
See application file for complete search history.

(56) References Cited

U.S. PATENT DOCUMENTS

| | | | |
|---|---|---|---|
| 4,222,921 A | 9/1980 | Van Eenam | |
| 4,528,347 A | 7/1985 | Harada et al. | |
| 4,605,701 A | 8/1986 | Harada et al. | |
| 4,614,593 A | 9/1986 | Roark | |
| 5,487,888 A | 1/1996 | Mandeville, III et al. | |
| 5,496,545 A | 3/1996 | Holmes-Farley et al. | |
| 5,589,166 A | 12/1996 | McTaggart et al. | |
| 5,607,669 A * | 3/1997 | Mandeville et al. | 424/78.12 |
| 5,618,530 A | 4/1997 | Mandeville, III et al. | |
| 5,624,963 A | 4/1997 | Mandeville, III et al. | |
| 5,667,775 A | 9/1997 | Holmes-Farley et al. | |
| 5,679,717 A | 10/1997 | Mandeville, III et al. | |
| 5,693,675 A | 12/1997 | Mandeville, III et al. | |
| 5,702,696 A | 12/1997 | Mandeville, III et al. | |
| 5,703,188 A | 12/1997 | Mandeville, III et al. | |
| 5,900,475 A | 5/1999 | Mandeville, III et al. | |
| 5,925,379 A | 7/1999 | Mandeville, III et al. | |
| 6,083,495 A | 7/2000 | Holmes-Farley et al. | |
| 6,083,497 A | 7/2000 | Huval et al. | |
| 6,177,478 B1 | 1/2001 | Holmes-Farley et al. | |
| 6,180,754 B1 * | 1/2001 | Stutts et al. | 528/422 |
| 6,203,785 B1 | 3/2001 | Holmes-Farley et al. | |
| 6,733,780 B1 * | 5/2004 | Tyler et al. | 424/464 |

FOREIGN PATENT DOCUMENTS

| | | |
|---|---|---|
| EP | 0 997 148 A1 | 5/2000 |
| JP | 2003183168 A * | 3/1998 |
| JP | 2003183168 * | 7/2003 |
| WO | WO96/21454 | 7/1996 |
| WO | WO-98/57652 * | 12/1998 |
| WO | WO98/57652 * | 12/1998 |
| WO | WO99/22743 | 5/1999 |
| WO | WO99/40990 | 8/1999 |

* cited by examiner

*Primary Examiner*—Zohreh A Fay
(74) *Attorney, Agent, or Firm*—Christopher M. Beck

(57) ABSTRACT

Disclosed is a pharmaceutical composition comprising a stable polyallylamine hydrochloride polymer in which between about 4% to about 12% by weight of the polymer is a chloride anion and a pharmaceutically acceptable carrier or diluent.

7 Claims, No Drawings

LOW SALT FORMS OF POLYALLYLAMINE

RELATED APPLICATIONS

This application claims the benefit of U.S. Provisional Application No. 60/284,445, filed on Apr. 18, 2001.

The entire teachings of the above application are incorporated herein by reference.

BACKGROUND OF THE INVENTION

Polyallylamine polymers have found many uses in recent years as therapeutic agents. For example, polyallylamines have been reported to be effective in treating patients with elevated serum phosphate levels and hyperphosphatemia (e.g., U.S. Pat. Nos. 5,496,545 and 5,667,775). Elevated serum phosphate is often present in patients with renal insufficiency, hypoparathyroidism, acute untreated acromegaly and overmedication with therapeutics comprising phosphate salts. Polyallylamines have also found uses as bile acid sequestrants (e.g., U.S. Pat. Nos. 5,624,963, 5,703,188, 5,840,766 and 6,060,517) and for lowering uric acid levels (U.S. Pat. No. 5,985,938). Of particular note is the drug Sevelamer Hydrochloride (Sevelamer), which has been approved by the Food and Drug Administration to treat hyperphosphatemia.

The characteristic structural feature of a polyallylamine polymer is the presence of repeat units from polymerized allylamine monomer. For example, Sevelamer is a homopolymer comprising repeat units in which the amine nitrogen from the polymerized allylamine monomer is unsubstituted. The structure of the repeat unit from the Sevelamer homopolymer is shown below in Structural Formula (I):

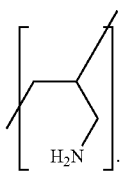

(I)

In other polyallylamines, the amine nitrogen in the polymerized allyl monomer repeat units is substituted. Suitable substituents are described below.

To maintain potency and prevent undesired side effects, it is critically important that the ingredients in a pharmaceutical product, including the pharmacologically active ingredient, are chemically stable over extended time periods, typically for at least two years. During this time, decomposition rates must be within acceptable limits. However, amine compounds are susceptible to oxidative decomposition. For this reason, drugs containing amine functional groups are generally stored and administered in the form of a salt, typically a hydrochloride (HCl) salt, which, in most cases, is more stable than the corresponding free amine. Sevelamer, for example, is stored and administered as a salt in which about 40% of the amine groups are protonated as the hydrochloride salt (about 18% by weight of the polymer is chloride).

SUMMARY OF THE INVENTION

Surprisingly, it has now been found that amine-containing polymers in which significantly less than 40% of the amine group are protonated decompose at rates that are within acceptable limits for drug stability purposes. The art has established guidelines for drug stability testing which include: International Conference on Harmonization (ICH), Section Q1A "Stability Testing of New Drug Substances and Products" (Revised) and; the Code of Federal Regulations (CFR), 21 CFR 211.166 "Guideline for Submitting Documentation for the Stability of Human Drugs and Biologics". For example, it has been shown that under accelerated stability testing conditions, polyallylamine hydrochloride with between about 4.0% by weight of chloride to about 12% by weight of chloride can be stored for at least two years with minimal decomposition. In addition, this "low chloride" or "low salt" form of polyallylamine hydrochloride possesses the same desirable therapeutic and formulation properties as do the corresponding polymers with higher levels of chloride. Based on the foregoing discoveries, stable pharmaceutical formulations of polyallylamine polymers with low levels of protonation and novel pharmaceutical compositions comprising said polymers are disclosed herein. As used herein, the term "stable" with reference to the polymer and its pharmaceutical formulation means that the pharmaceutical formulation of the polymer decomposes at rates that are within acceptable limits for drug stability purposes, while maintaining therapeutic effectiveness.

One embodiment of the present invention is a stable, polyallylamine polymer wherein about 9.0% to about 27.0% of the amine groups in the polyallylamine polymer are protonated (e.g., polyallylamine hydrochloride with between about 4.0% by weight and about 12.0% by weight of the polymer is chloride anion). More preferably, between about 11% to about 20.0% of the amine groups in the polyallylamine polymer are protonated (e.g., polyallylamine hydrochloride with between about 5.0% by weight and about 9.0% by weight of the polymer is chloride anion). The amine groups are preferably protonated with as a hydrochloride salt.

Another embodiment of the present invention is a pharmaceutical composition comprising the stable polyallylamine polymer described above and a pharmaceutically acceptable carrier or diluent.

The low salt form of polyallylamine has important therapeutic and drug formulation advantages compared with the corresponding polymer having higher levels of salt. For example, polyallylamines are commonly used to reduce phosphate serum levels in patients with renal failure. Unfortunately, most patients with renal failure also suffer from low blood pH or "acidosis". Low salt forms of polyallylamine have less anions to release into the blood and possess an increase in the number of unprotonated, basic amines compared with higher salt forms of the polymer, and thereby would tend to increase blood pH. Secondly, low salt content decreases the weight and bulk of the ultimate dosage form, thereby making it easier to formulate and administer.

DETAILED DESCRIPTION OF THE INVENTION

A polyallylamine is a polymer having repeat units from polymerized allyl amine monomer(s). The amine group of an allyl monomer can be unsubstituted or substituted with, for example, one or two a $C_1$-$C_{10}$ straight chain or branched alkyl groups. The alkyl group(s) is optionally substituted with one or more hydroxyl, amine, halo, phenyl, amide or nitrile groups. Preferably, the polyallylamine polymers of the present invention comprise repeat units represented by Structural Formula (I):

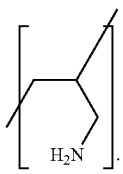

A polyallylamine can be a copolymer comprising repeat units from two or more different polymerized allyl monomers or with repeat units from polymerized allyl monomer(s) and repeat units from polymerized non-allyl monomer(s). Examples of suitable non-allyl monomers include acrylamide monomers, acrylate monomer, maleic acid, malimide monomers, vinyl acylate monomers and alkyl substituted olefines. Preferably, however, the polyallylamines of the present invention comprise repeat units solely from polymerized allyl amine monomer. More preferably, the polyallylamine polymers of the present invention are homopolymers. Even more preferably, the polyallylamine polymers of the present invention are homopolymers of repeat units represented by Structural Formula (I).

Although a polyallylamine can be uncrosslinked, it is preferably crosslinked. Suitable crosslinking agents include epichlorohydrin, 1,4 butanedioldiglycidyl ether, 1,2 ethanedioldiglycidyl ether, 1,3-dichloropropane, 1,2-dichloroethane, 1,3-dibromopropane, 1,2-dibromoethane, succinyl dichloride, dimethylsuccinate, toluene diisocyanate, acryloyl chloride, and pyromellitic dianhydride. Epichlorohydrin is a preferred crosslinking agent. Typically, between about 9% and about 30% of the allylic nitrogen atoms are bonded to a crosslinking group, preferably between 15% and about 21%. Preferably, epichlorohydrin is the crosslinking agent, resulting in 2-hydroxypropyl crosslinking groups.

Polyallylamines can be protonated with organic or inorganic acids comprising physiologically acceptable anions. The anions can be partially or completely replaced with other physiologically acceptable anions by various means, including by passing the polymer over an anion exchange resin prior to crosslinking. A polyallyamine polymer can comprise more than one type of anion. Examples of suitable inorganic anions include halide (especially chloride), carbonate, bicarbonate, sulfate, bisulfate, hydroxide, nitrate, persulfate and sulfite. Suitable organic ions include acetate, ascorbate, benzoate, citrate, dihydrogen citrate, hydrogen citrate, oxalate, succinate, tartrate, taurocholate, glycocholate, and cholate. Chloride is a preferred anion.

In a preferred embodiment, the polyallyamine polymer is crosslinked with epichlorohydrin and between about 9% to about 30% (preferably about 15% to about 21%) of the allylic nitrogen atoms are bonded to a crosslinking group and the anion is chloride. More preferably, the polyallylamine polymer is a homopolymer. Even more preferably, the polyallylamine polymer is a homopolymer comprising repeat units represented by Structural Formula (I).

In a most preferred embodiment, the polyallylamine polymer is homopolyallyamine crosslinked with about 9.0-9.8% epichlorohydrin, preferably 9.3-9.5%, and is the active chemical component of the drug known as Sevelamer HCl.

The polyallylamine polymers described herein are useful for treating a variety of conditions, including hyperphosphatemia (e.g., patients with high serum phosphate levels such as patients with end stage renal disease, hypoparathyroidism, acromegaly, and overmedication with phosphate salts). The polymers described herein are also suitable as bile acid sequestrants, in the treatment of Wilson's Disease, for lowering uric acid levels in a patient, and in the prevention of thrombosis of shunts such as those that may be used in conjunction with renal dialysis. Dosages of between about 0.5 gram/day and about 10 grams/day are typical, and preferably between about 3 grams/day and about 6 grams/day.

The polymer can be administered alone or in a pharmaceutical composition comprising the polymer, a pharmaceutically acceptable carrier or diluent, and optionally, one or more additional drugs. The polymers are preferably administered orally and even more preferably administered orally with a meal. Suitable carriers and diluents will be immediately apparent to persons skilled in the art. These carrier and diluent materials, either inorganic or organic in nature, include, for example, silicon oxide, stearic acid, gelatin, albumin, lactose, starch, magnesium stearate preservatives (stabilizers), melting agents, emulsifying agents, salts and buffers. The therapeutically effective amount can be administered in a series of doses separated by appropriate time intervals such as minutes or hours.

Further descriptions of suitable dosages, dosages forms and routes of administration are provided in U.S. Pat. Nos. 5,496,545, 5,667,775 6,083,495, 5,702,696 and 5,487,999. The entire teachings of these patents are incorporated herein by reference.

The invention is illustrated by the following examples which are not intended to be limiting in any way.

EXAMPLES

Example 1

Preparation of Low Chloride Sevelamer Hydrochloride (Polyallylamine Homopolymer)

Sevelamer HCl of various chloride levels (~1%, ~5%, ~9% by weight) was prepared from commercial bulk Sevelamer (~18% chloride by weight) manufactured by Dow Chemicals (Midland, Mich.). The bulk Sevelamer was slurried in water, and further neutralized with 50% aqueous sodium hydroxide (NaOH) solution. Varying amounts of NaOH were added to achieve the desired reduction in the level of chloride by weight of the polymer. For example, 0.5 equivalents of NaOH added with respect to the total chloride in Renagel (~18%), yields approximately 50% reduction in chloride resulting in Sevelamer having about 9% chloride by weight of the polymer, 0.75 equivalents of NaOH yields approximately a 75% reduction in chloride resulting in Sevelamer having about 5% chloride by weight, and 0.95 equivalents or higher resulted in Sevelamer having about 1% chloride by weight.

Neutralized Sevelamer was filtered and resuspended in an adequate amount of water such that conductive slurry is less than 1 mS/cm. The suspension was filtered and placed dried in a 70° C. forced air oven until it was dried. The dried Sevelamer was then ground and sieved.

Alternatively, polyallylamine polymers crosslinked with epichlorohydrin may be synthesized as described in U.S. Pat. Nos. 5,496,545, 5,667,775 6,083,495, 5,702,696 and 5,487,999, and neutralized as described above to yield the desired percentage of chloride by weight of the polymer.

Example 2

Stability Studies with Low Chloride Sevelamer HCl

The low chloride Sevelamer Hydrochloride polymers (a polyallylamine homopolymer) described in Example 1 having approximately 9%, 5%, and 1% chloride by weight of the polymer respectively, were tested for stability in accordance with the guidelines of the International Conference on Harmonization (ICH). The accelerated stability tests included placing each of the respective low chloride polymer samples, in an oven at 40 C with 75% relative humidity for 1, 2, 3 and 6 months. At each time point, a portion of each respective polymer sample was removed and analyzed using two assays, the phosphate binding assay and the soluble oligomers assay. Both assays are demonstrated as stability indicating assays for polyallylamine polymers.

The phosphate binding assay determines the phosphate binding capacity of Sevelamer Hydrochloride, which is an indicator of its therapeutic effectiveness. The assay is performed by mixing the Sevelamer Hydrochloride samples with a solution of known phosphate concentration, filtering off the polymer-phosphate complex and quantitating the unbound phosphate concentration by ion chromatography.

The soluble oligomers assay determines the amount of soluble oligomers in each Sevelamer Hydrochloride sample. Titratable amine and soluble oligomer content are indicative of polymer stability at each time point. The assay is performed by reacting ninhydrin with oligomers that have been extracted from samples of Sevelamer Hydrochloride at each respective time point. Spectrophotometric quantitation to determine the amount of residual soluble oligomers was performed by comparing the absorbance of the derivatized sample extract to the absorbance of known standards.

The results of the stability testing demonstrate that the 9% and 5% chloride composition by weight samples, have very good stability profiles (meaning they retain the ability to bind phosphate and the residual soluble oligomer levels are within acceptable limits for each sample). The results of this study indicate that low chloride versions of Sevelamer Hydrochloride with 9% and 5% chloride composition by weight respectively, have stability profiles that are similar to Sevelamer Hydrochloride having approximately 18% chloride content (the chloride content found in the currently marketed Sevelamer drug product). The accelerated stability results further indicate that the shelf life of a low chloride Sevelamer Hydrochloride drug product is the equivalent of at least 2 years.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising a pharmaceutically acceptable carrier or diluent and a stable polyallylamine hydrochloride polymer wherein between about 4% to about 12% by weight of the polymer is chloride anion and between about 9.0% to about 27.0% of the amine groups in the polyallylamine polymer are protonated.

2. The pharmaceutical composition of claim 1 wherein between about 5% to about 9% by weight of the polymer is chloride anion.

3. The pharmaceutical composition of claim 2 wherein the polymer is a homopolymer.

4. The pharmaceutical composition of claim 3 wherein the polyallylamine hydrochloride polymer comprises a repeat unit represented by Structural Formula (I):

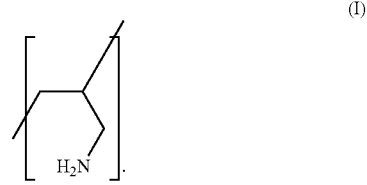

5. The pharmaceutical composition of claim 4 wherein the polymer is crosslinked.

6. The pharmaceutical composition of claim 5 wherein the polymer is crosslinked with 2-hydroxypropyl crosslinking groups.

7. A pharmaceutical composition comprising a pharmaceutically acceptable carrier or diluent and a stable polyallylamine homopolymer comprising repeat units represented by Structural Formula (I):

wherein the homopolymer is crosslinked with 2-hydroxypropyl groups, between about 9% and about 30% of the amine groups in the homopolymer are bonded to one of the 2-hydroxypropyl crosslinking groups, and between about 5% and about 9% by weight of the homopolymer is chloride anion and between about 9.0% to about 27.0% of the amine groups in the polyallylamine polymer are protonated.

* * * * *